United States Patent [19]

Cohen

[11] Patent Number: 5,984,954
[45] Date of Patent: Nov. 16, 1999

[54] METHODS AND APPARATUS FOR R-WAVE DETECTION

[75] Inventor: Alan M. Cohen, Arlington, Mass.

[73] Assignee: Boston Medical Technologies, Inc., Wakefield, Mass.

[21] Appl. No.: 08/940,396

[22] Filed: Oct. 1, 1997

[51] Int. Cl.⁶ .................................................. A61B 5/0456
[52] U.S. Cl. ............................................................ 607/521
[58] Field of Search ................................. 600/513, 509, 600/521

[56] References Cited

U.S. PATENT DOCUMENTS

| | | | |
|---|---|---|---|
| 2,649,573 | 8/1953 | Goldberg et al. | 324/71 |
| 3,142,796 | 7/1964 | Goldberg et al. | 324/71 |
| 3,340,867 | 9/1967 | Kubicek et al. | 128/2.05 |
| 3,407,818 | 10/1968 | Costanzo | 128/384 |
| 3,560,845 | 2/1971 | Goldberg et al. | 324/34 |
| 3,731,184 | 5/1973 | Goldberg et al. | 324/34 R |
| 3,925,762 | 12/1975 | Heitlinger et al. | 340/150 |
| 3,991,304 | 11/1976 | Hillsman | 235/151.34 |
| 4,023,563 | 5/1977 | Reynolds et al. | 128/2.05 R |
| 4,031,885 | 6/1977 | Davis et al. | 128/2.08 |
| 4,036,215 | 7/1977 | Doll | 128/2.05 F |
| 4,137,910 | 2/1979 | Murray | 128/2.05 R |
| 4,216,779 | 8/1980 | Squires et al. | 128/682 |
| 4,240,442 | 12/1980 | Andresen et al. | 128/708 |
| 4,308,872 | 1/1982 | Watson et al. | 128/725 |
| 4,346,718 | 8/1982 | Morris | 128/710 |
| 4,364,397 | 12/1982 | Citron et al. | 128/710 |
| 4,367,753 | 1/1983 | Jirak . | |
| 4,408,614 | 10/1983 | Weaver et al. | 128/680 |
| 4,433,693 | 2/1984 | Hochstein | 128/721 |
| 4,440,177 | 4/1984 | Anderson et al. | 128/719 |
| 4,446,872 | 5/1984 | Marsoner et al. | 128/700 |
| 4,506,678 | 3/1985 | Russell et al. | 128/723 |
| 4,513,295 | 4/1985 | Jones et al. | 346/33 ME |
| 4,559,947 | 12/1985 | Renger et al. | 128/419 PG |
| 4,589,420 | 5/1986 | Adams et al. | 128/702 |
| 4,649,929 | 3/1987 | Weaver et al. | 128/680 |
| 4,679,144 | 7/1987 | Cox et al. | 364/417 |
| 4,692,148 | 9/1987 | Kantrowitz et al. | 604/96 |
| 4,721,114 | 1/1988 | DuFault et al. | 128/696 |
| 4,777,960 | 10/1988 | Berger et al. | 128/706 |
| 4,807,640 | 2/1989 | Watson et al. | 128/721 |
| 4,819,654 | 4/1989 | Weaver et al. | 128/680 |
| 4,832,038 | 5/1989 | Arai et al. | 128/670 |
| 4,862,361 | 8/1989 | Gordon et al. | 364/413.06 |
| 4,869,262 | 9/1989 | Orr et al. | 128/672 |
| 4,870,974 | 10/1989 | Wang | 128/700 |
| 4,889,131 | 12/1989 | Salem et al. | 128/671 |
| 4,905,708 | 3/1990 | Davies | 128/705 |
| 4,909,260 | 3/1990 | Salem et al. | 128/721 |
| 4,913,146 | 4/1990 | DeCote, Jr. | 128/419 PG |
| 4,930,517 | 6/1990 | Cohen et al. | 128/671 |
| 4,934,377 | 6/1990 | Bova et al. | 128/696 |
| 4,947,857 | 8/1990 | Albert et al. | 128/696 |

(List continued on next page.)

FOREIGN PATENT DOCUMENTS

| | | | |
|---|---|---|---|
| 1391616 | 4/1988 | Russian Federation | A61B 5/04 |
| 2113101 | 8/1983 | United Kingdom | A61M 16/00 |
| WO 9712546 | 4/1997 | WIPO | A61B 5/0245 |

*Primary Examiner*—Jeffrey R. Jastrzab
*Attorney, Agent, or Firm*—Daly, Crowly & Mofford, LLP

[57] ABSTRACT

Apparatus and methods for determining the precise times of occurrence of R-waves in an ECG signal of a patient. Samples of the patient's ECG signal are accumulated and an ECG window comprising a predetermined number of the samples is defined. In accordance with one embodiment of the invention, the patient's blood pressure signal is processed to detect systoles and the ECG window has a predetermined time relationship to detected systoles. In accordance with an alternative embodiment, the ECG signal is first processed to approximate the times of occurrence of R-waves and the ECG window is defined to have a predetermined time relationship to the approximated R-wave times. ECG signal samples within the ECG window are processed to determine a maximum and the time of occurrence of the maximum is stored as the time of an R-wave event.

13 Claims, 9 Drawing Sheets

U.S. PATENT DOCUMENTS

| | | | |
|---|---|---|---|
| 4,974,597 | 12/1990 | Walloch | 600/493 |
| 4,979,110 | 12/1990 | Albrecht et al. | 364/413.03 |
| 4,984,158 | 1/1991 | Hillsman | 364/413.04 |
| 5,025,794 | 6/1991 | Albert et al. | 128/696 |
| 5,027,824 | 7/1991 | Dougherty et al. | 128/702 |
| 5,148,812 | 9/1992 | Verrier et al. | 128/704 |
| 5,156,148 | 10/1992 | Cohen | 128/419 PG |
| 5,159,935 | 11/1992 | Sackner et al. | 128/721 |
| 5,167,506 | 12/1992 | Kilis et al. | 434/262 |
| 5,269,301 | 12/1993 | Cohen | 607/6 |
| 5,277,189 | 1/1994 | Jacobs | 128/696 |
| 5,285,793 | 2/1994 | Slovut et al. | 128/706 |
| 5,299,119 | 3/1994 | Kraf et al. | 364/413.06 |
| 5,301,678 | 4/1994 | Watson et al. | 128/721 |
| 5,312,441 | 5/1994 | Mader et al. | 607/5 |
| 5,316,008 | 5/1994 | Suga et al. | 128/700 |
| 5,330,508 | 7/1994 | Gunderson | 607/14 |
| 5,333,106 | 7/1994 | Lampher et al. | 364/413.01 |
| 5,339,822 | 8/1994 | Taylor et al. | 600/513 |
| 5,360,008 | 11/1994 | Campbell, Jr. | 128/671 |
| 5,390,679 | 2/1995 | Martin | 128/673 |
| 5,394,873 | 3/1995 | Kraemer et al. | 128/653.2 |
| 5,400,795 | 3/1995 | Murphy et al. | 128/702 |
| 5,423,325 | 6/1995 | Burton | 128/702 |
| 5,437,285 | 8/1995 | Verrier et al. | 128/702 |
| 5,450,850 | 9/1995 | Iinuma | 128/661.09 |
| 5,485,847 | 1/1996 | Baker, Jr. | 128/666 |
| 5,497,778 | 3/1996 | Hon | 128/672 |
| 5,509,404 | 4/1996 | Lloyd et al. | 128/200.14 |
| 5,520,190 | 5/1996 | Benedict et al. | 128/700 |
| 5,543,012 | 8/1996 | Watson et al. | 156/440 |
| 5,570,696 | 11/1996 | Arnold et al. | 128/707 |
| 5,724,580 | 3/1998 | Levin et al. | 395/615 |

METHODS AND APPARATUS FOR R-WAVE DETECTION

CROSS-REFERENCE TO RELATED APPLICATIONS

Not applicable.

STATEMENTS REGARDING FEDERALLY SPONSORED RESEARCH

Not applicable.

BACKGROUND OF THE INVENTION

An electrocardiogram (ECG or, sometimes, EKG) signal is an electrical signal indicative of changes in electrical potential during a heartbeat, or contraction of the heart. ECG signals include features corresponding to certain aspects of each heartbeat and are used to diagnose cardiac activity abnormalities. One such feature is the R-wave which is manifested as a positive voltage spike in the ECG signal coincident with a ventricular contraction.

Various medical diagnostic and treatment apparatus require detection of the time of occurrence of the R-waves of a patient's ECG signal, including heart rate monitors and heart rate variability monitors. Heart rate variability monitors refer to a class of instruments with which changes in heartbeat rate are measured.

Conventional R-wave detection is typically achieved with a threshold detection scheme by which the ECG signal is compared to a threshold value, with the occurrence of the ECG signal exceeding the threshold indicating the occurrence of an R-wave. R-wave detection is complicated by the inherent noise and other artifacts typically associated with an ECG signal. For this reason, the ECG signal is typically filtered prior to comparison with the threshold value.

The threshold detection method of detecting R-waves is often suitable for use in heart rate monitors, since such monitors generally provide a gross measure of heart rate which is subject to drift. However, threshold detection for detecting R-waves is less satisfactory for use in heart rate variability monitors, since detection of precise R-wave times is critical to providing an accurate heart rate variability indication.

In one conventional heart rate variability monitor, sold by Boston Medical Technologies under the product name HRView™ versions I and II, R-wave detection is achieved with a combination of filtering, threshold detection and operator interaction. Once "approximate" R-wave locations are detected by threshold detection, the operator views the ECG signal and approximate R-wave locations on a display and is able to remove R-wave detections which are likely to be false based on some criteria, such as the detections being too close in time to other detections. The user is also able to view a heart rate variability signal (i.e., heart rate versus time) generated in response to the detected R-waves and remove any heart rate variations which are likely to be false based on some criteria, such as the magnitude of the variation. This technique is referred to as "splining" since, in response to a user's indication that a particular heart rate variation exceeds some criteria, the heart rate variability signal is "splined," so as to bridge the signal across the particular heart rate variation.

It would be desirable to provide apparatus and techniques for detecting R-wave events with improved accuracy, particularly for use in heart rate variability monitors which rely heavily on precise R-wave detection.

BRIEF SUMMARY OF THE INVENTION

The invention relates to methods and apparatus for detecting the times of occurrence of R-wave events of a patient's ECG signal in response to the patient's blood pressure signal and/or the patient's ECG signal. In general, an ECG window of the ECG signal in which an R-wave event is expected to occur is defined for processing and the maximum signal sample within the ECG window is determined and stored as the precise time of an R-wave.

In a first processing stage, the times of occurrence of R-waves of the ECG signal are approximated. Thereafter, in a second processing stage, the approximate R-wave times are used to define the ECG windows which are then processed to determine the precise R-wave times. With this arrangement, the definition and precise processing of signal samples within the relatively narrow ECG windows in which the R-wave events occur makes precise R-wave detection possible, since such precise processing of the entire ECG signal is computationally intensive and infeasible.

In one embodiment, the R-waves of the ECG signal are detected in response to both the ECG signal and the blood pressure signal. More particularly, the blood pressure signal is processed to determine the time of occurrence of systoles, and the ECG window is defined to have a predetermined time relationship to the detected systoles.

In an alternative embodiment, the R-waves of the ECG signal are detected in response to only the ECG signal which is initially processed by filtering and threshold detection in order to determine the approximate times of occurrence of the R-waves. The ECG window is defined to have a predetermined time relationship to the approximate R-wave times.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
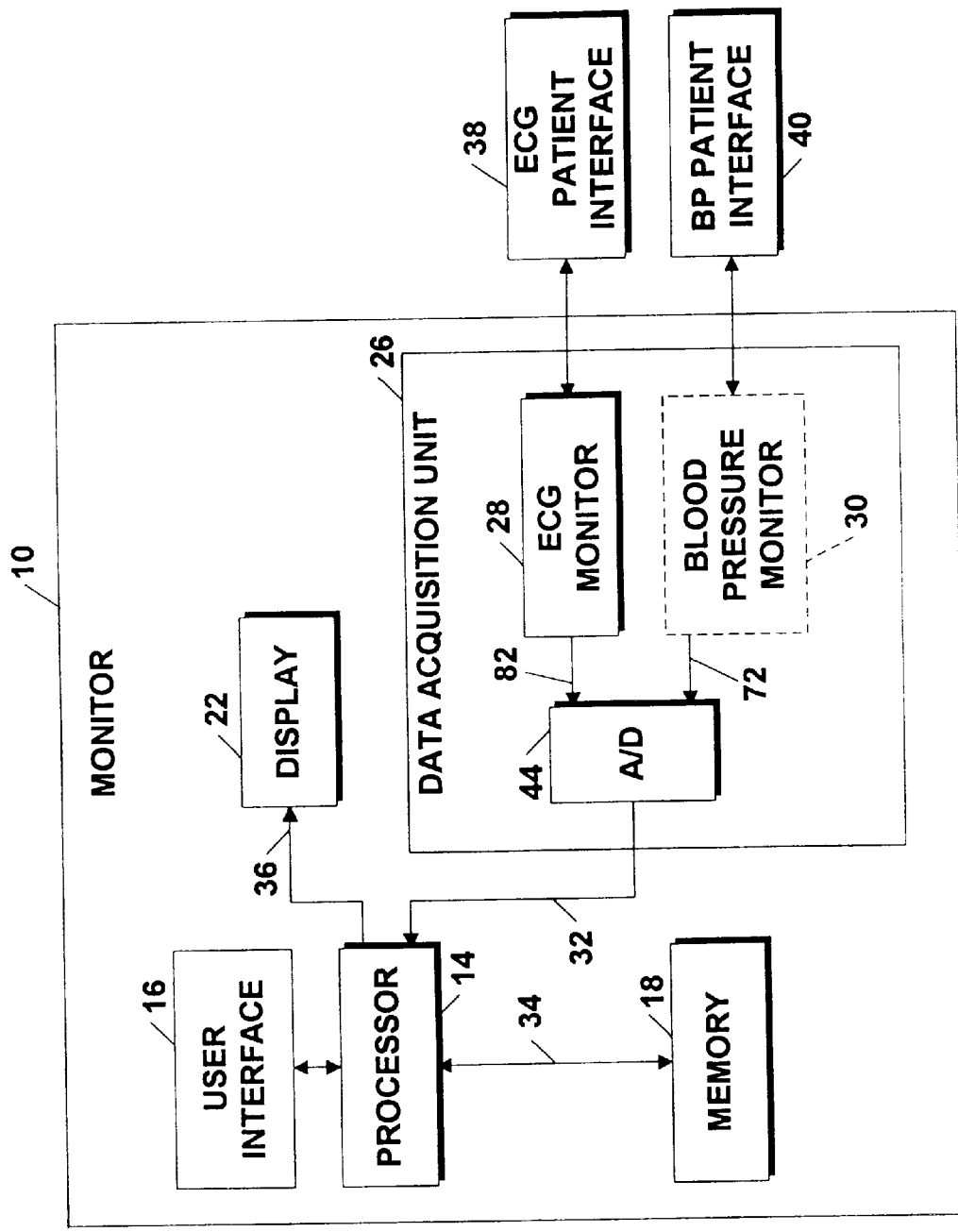
FIG. 1 is a block diagram of a monitor including features of the invention.

Referring to FIG. 1, a block diagram of a monitor 10 includes a processor 14 for detecting the location of the R-waves of a patient's ECG signal, a memory 18, a display 22 and a data acquisition unit 26. The R-wave detection apparatus and techniques described and claimed herein are particularly well-suited for use in heart rate variability monitors, which rely on precise R-wave detection. More generally, however, the monitor 10 detects the location of R-waves of a patient's ECG signal and it will be appreciated by those of ordinary skill in the art that the apparatus and techniques described herein are suitable for use with other types of medical monitors.

The data acquisition unit 26 includes an ECG monitor 28 and, optionally, may further include a blood pressure monitor 30. The ECG monitor 28 operates with a conventional ECG patient interface 38, such as electrode pads adapted for attachment to a patient's chest, and includes signal processing circuitry for conditioning the measured ECG signal for further processing. One suitable commercially available ECG monitor is of the type sold by Serena Medical Electronics Co., Inc. of San Jose, Calif. under the product name ECG Isolation Amplifier Module Model ECG-170. The output of the ECG monitor 28 is an amplified ECG signal 82 which is converted into a digital signal 32 by an analog-to-digital converter 44.

Like the ECG monitor, the optional blood pressure monitor 30 is a conventional unit which is operative with a blood pressure patient interface 40, such as a blood pressure cuff or a pulse oximetry-type device located near an atrial line at various locations on the patient's body, such as near the heart, a finger or earlobe. The blood pressure monitor 30 includes signal processing circuitry, such as an amplifier and filter. The output of the blood pressure monitor 72 is an analog signal which is converted into a digital signal 32 by the analog-to-digital converter 44. One suitable commercially available blood pressure monitor is of the type sold by Colin Medical Instruments Corp. of San Antonio, Tex. under the product name Colin BP-508.

The digitized ECG and blood pressure signal 32 is coupled to the processor 14 for storage in the memory 18 via signal bus 34. While the illustrative monitor 10 stores digitized versions of the measured ECG and blood pressure signals (i.e., stores samples of the measured ECG and blood pressure signals), it will be appreciated by those of ordinary skill in the art that the analog ECG and blood pressure signals themselves may alternatively be stored in memory 18 for processing, including subsequent analog-to-digital conversion.

The processor 14 may take various forms, such as the microprocessor of a standard personal computer, workstation or other microprocessor-driven device. As one example, the processor 14 is an INTEL-compatible microprocessor of an IBM-compatible personal computer running the MICROSOFT WINDOWS graphical user interface, The memory 18 includes a Random Access Memory (RAM) and the user interface 16 may include a keyboard, touch screen and/or mouse. In the illustrative embodiment, the user interface 16 includes a touch screen incorporated into the display 22, the display is a flat panel LCD display of the type sold by Goldstar and the processor 14 and memory 18 are typical components associated with an IBM-compatible personal computer. It will be appreciated by those of ordinary skill in the art that the apparatus and techniques of the system 10 may be implemented on various equipment, both hardware and software.

In applications in which the monitor 10 is a heart rate variability monitor 10, the processor provides additional processing including preparing the digitized signals for further time domain and spectral analysis and interfacing with the display 22 via signal line, or bus 36 to cause various data and information to be displayed to the user, including the stored ECG and blood pressure signals. Further, the detected R-wave times are used by the processor 14 to generate a heart rate variability versus time signal which is likewise displayed to the user.

Figure 2:
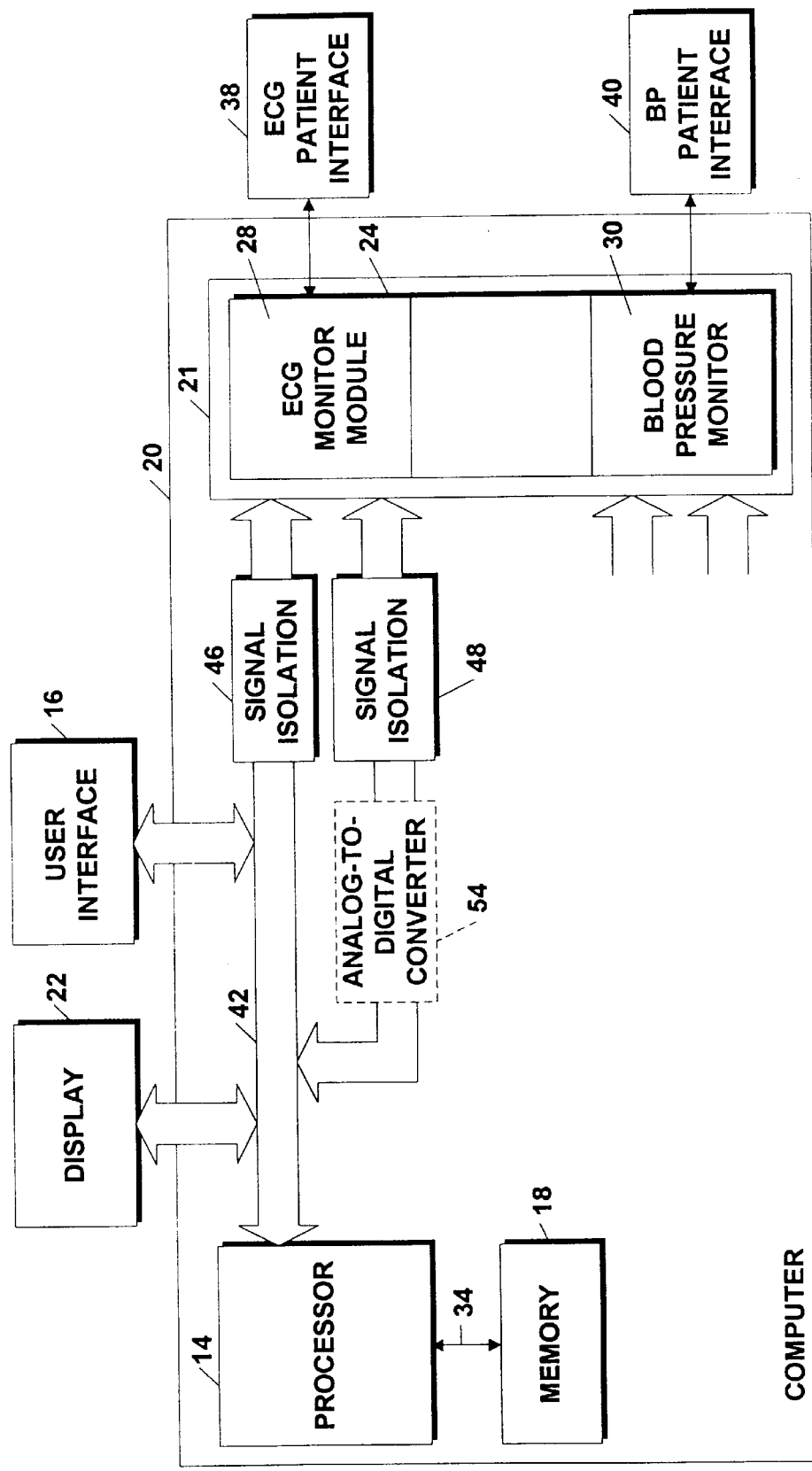
FIG. 2 is a block diagram of a computer-based implementation of the monitor of FIG. 1.

Referring to FIG. 2, the ECG monitor 28 and/or blood pressure monitor 30 may be implemented in the form of a "circuit module" adapted for insertion into an Input/Output (I/O) port or slot 21 of a standard personal computer chassis 20. To this end, the circuit modules 28, 30 are housed in a metal or metalized-plastic box, or instrument chassis 24, which is adapted for insertion into an opening of the computer chassis 20 typically used for a diskette drive, tape drive or CD-ROM drive.

The monitor 10 may include additional circuitry (not shown) for measuring various other physiological phenomena of the patient, such as inspiration volume, in which case such circuitry is implemented in the form of one or more additional circuit modules. The instrument chassis 24 has an open front face which permits insertion of one or more circuit module(s) therein. The front face of any unused portions of the instrument chassis is covered by metal or metalized panels. Advantageously, the instrument chassis serves as a "Gauss cage" to reduce electromagnetic interference (EMI).

With this arrangement, the processor 14 can communicate with and control the ECG monitor module 28 and the blood pressure monitor module 30 via the computer's standard busses and the circuit modules can draw on the power available to the computer components. The processor 14 transmits any control information to the circuit modules 28, 30 via the computer's digital control bus 42 and receives the digital ECG and blood pressure signal 32 (FIG. 1) via the computer's digital control bus 42. In applications in which the circuit modules 28, 30 do not include analog-to-digital converters, an analog-to-digital converter 54 may be provided to digitize the ECG and blood pressure signal. For safety reasons, it is preferable to isolate the computer bus 42 from the circuit modules 28, 30, for example, with opto-isolators 46, 48, respectively.

Figure 3:
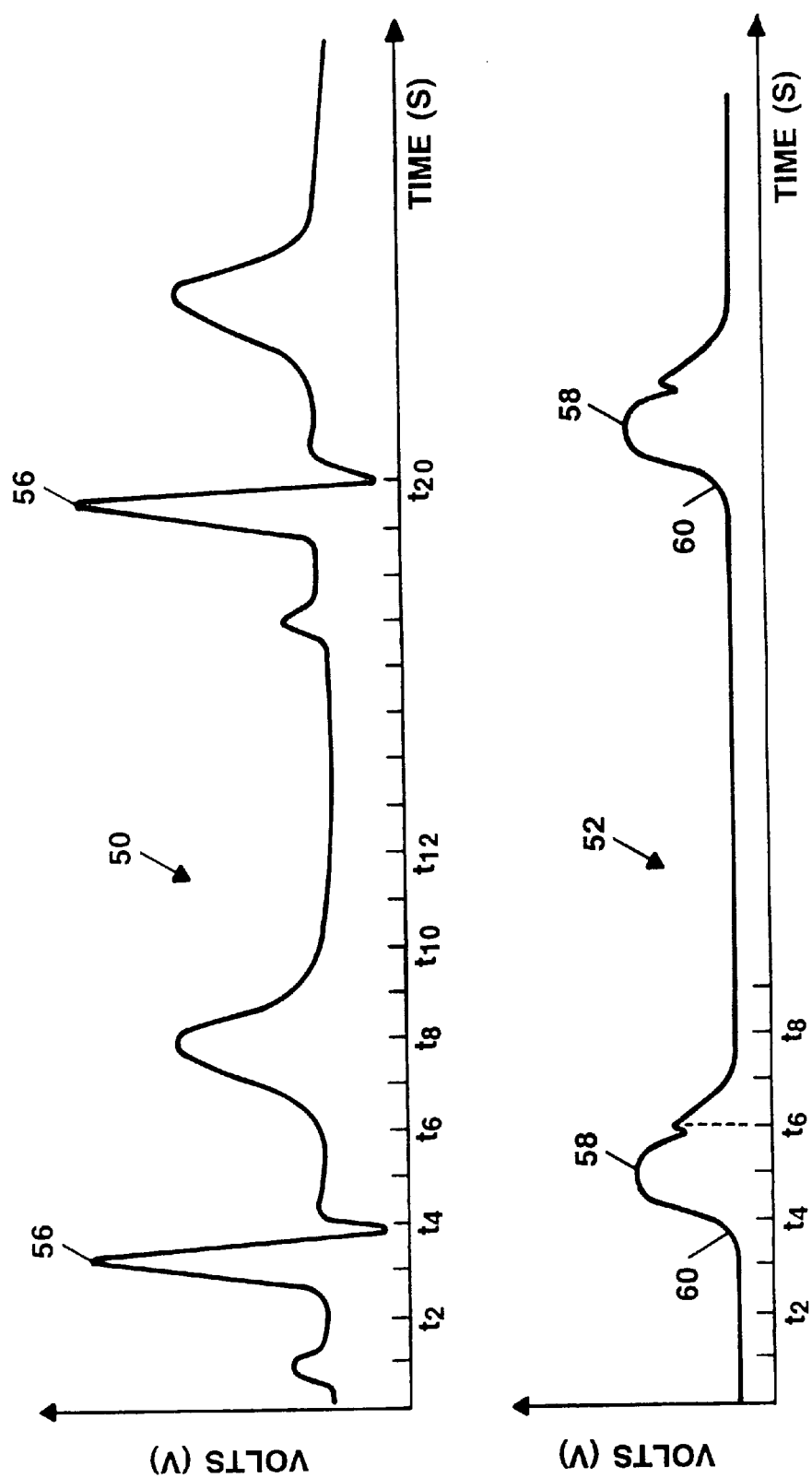
FIG. 3 illustrates typical ECG and blood pressure signals.

FIG. 3 illustrates a typical ECG signal 50 and a typical blood pressure signal 52, drawn to the same time scale. R-wave occurrences are labeled 56 on the ECG signal 50 and, on the blood pressure signal 52, systoles are labeled 58 and diastoles are labeled 60. It will be appreciated by those of ordinary skill in the art that each diastole 60 precedes an associated systole 58. The time scale is in seconds, with a typical duration of a blood pressure pulse (i.e., the duration between time $t_4$ and $t_7$) being approximately 0.5 seconds and a typical duration of an R-wave event 56 being on the order of 0.1 seconds.

As is apparent from the illustrative waveforms of FIG. 3, each R-wave event 56 precedes a blood pressure systole 58 by between approximately 50 and 200 milliseconds. As is further apparent from the waveforms, the attributes of the ECG signal 50 and the blood pressure signal 52 are periodic. However, the period of the features associated with these signals can and does vary in accordance with static attributes of the patient (e.g., the patient's weight) and dynamic attributes of the patient (e.g., physical exertion of the patient).

Figure 4:
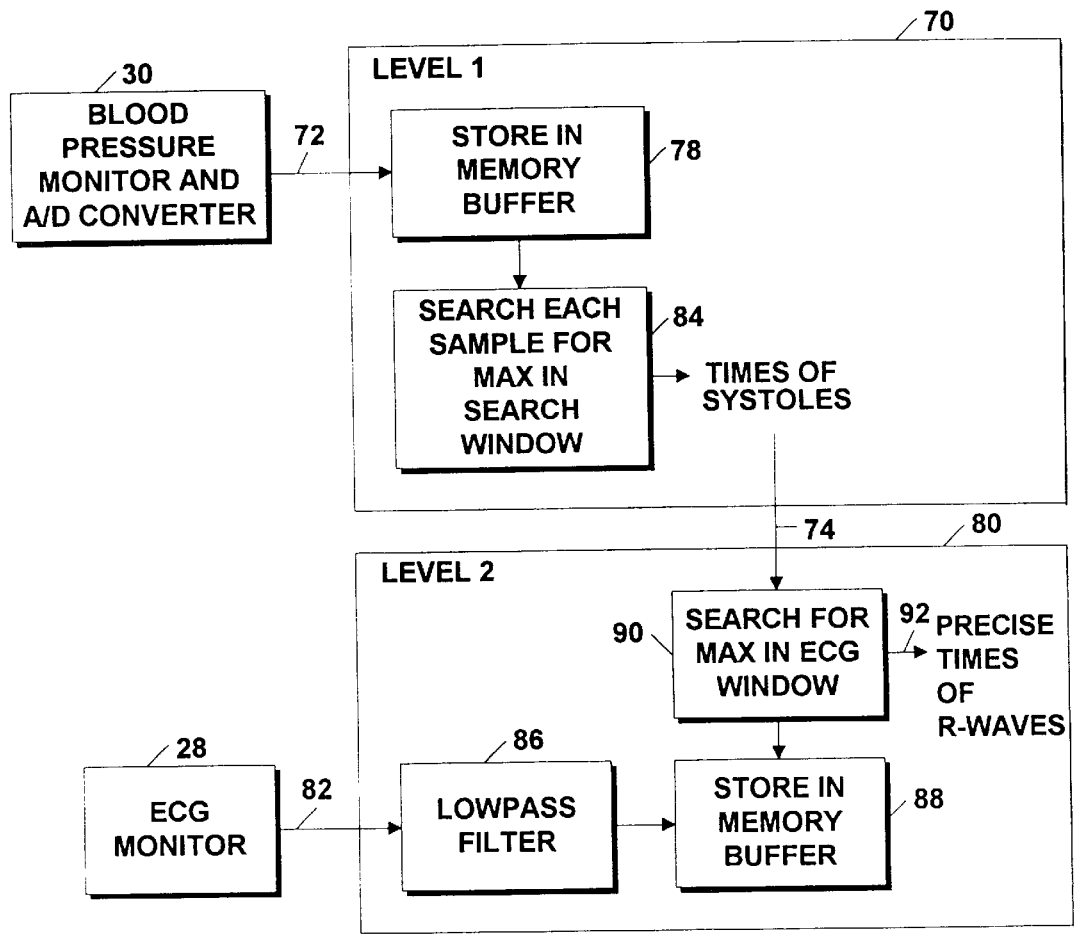
FIG. 4 is a block diagram of the overall process of R-wave detection in response to an ECG signal and a blood pressure signal according to the invention.

Referring to FIG. 4, a diagram illustrating one R-wave detection technique according to the invention is shown. In a first level, or stage 70 of R-wave detection, approximate times of systoles in the digitized blood pressure signal 72 are determined. A second level 80 of R-wave detection is responsive to the digitized ECG signal 82 for providing data 92 indicative of the precise time of occurrence of R-waves in the patient's ECG signal 82.

The technique illustrated by FIG. 4 will be described in greater detail in conjunction with the flow diagrams of FIGS. 5 and 6. In general, the blood pressure signal 72 is stored in a memory buffer as illustrated by step 78. In step 84, the memory is accessed and a maximum signal level within a search window is detected. The detected maximum within a plurality of search windows comprise the systole times as represented by output 74.

In accordance with the second level 80 of R-wave detection, the ECG signal 82 provided by monitor 28 is filtered in step 86, such as with a lowpass filter. The filtered ECG signal is then stored in a memory buffer in step 88. In step 90, an ECG window of the ECG signal is defined and searched in order to determine its maximum. It is these maxima within a plurality of ECG windows that collectively comprise the precise times of R-waves of the patient's ECG signal as represented by output 92.

Figure 5:
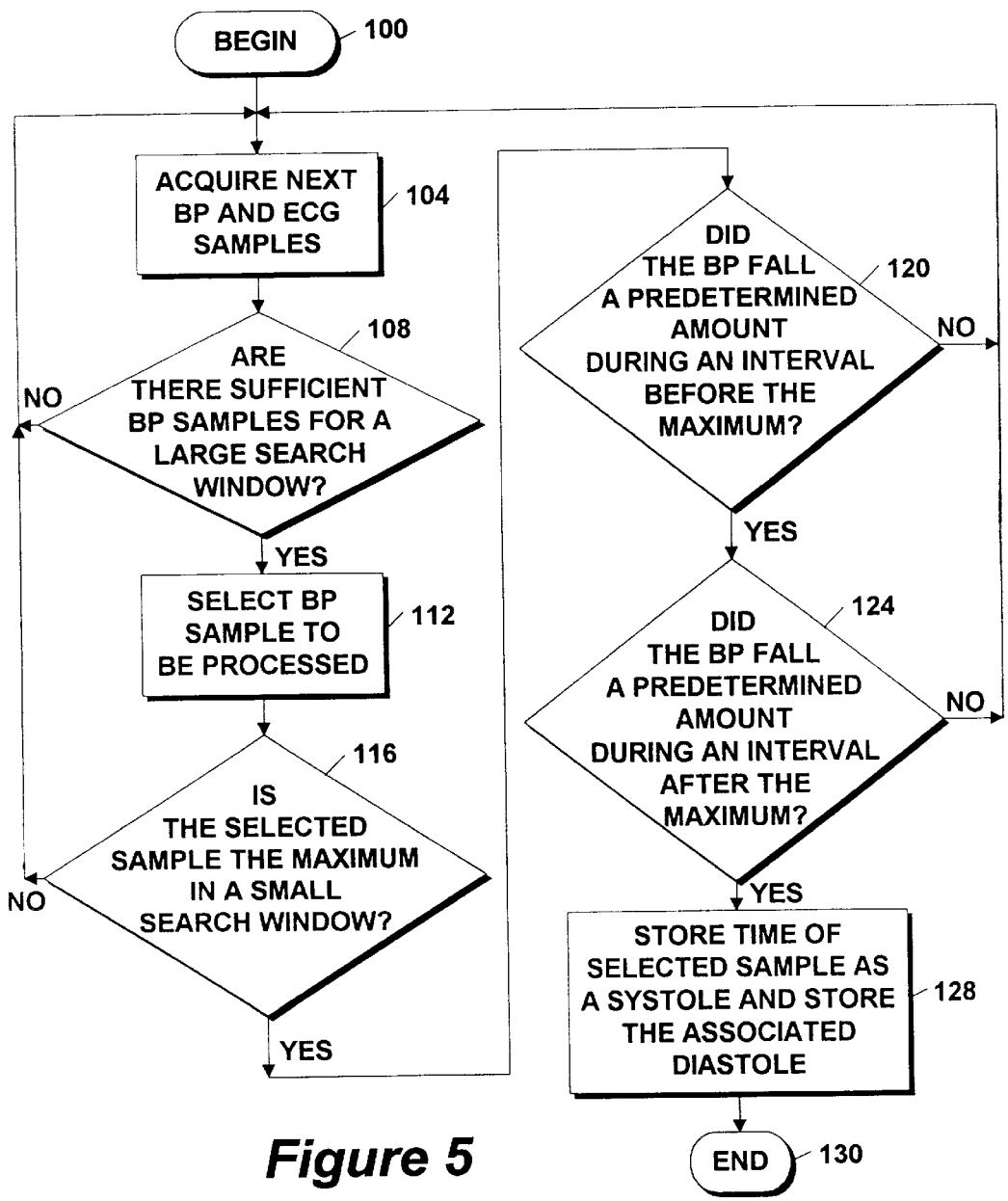
FIG. 5 is a flow diagram illustrating a method of implementing the first stage of R-wave detection of FIG. 4.

FIG. 5 illustrates one technique for implementing the first stage 70 of R-wave detection of FIG. 4. The process commences in step 100, following which a blood pressure signal sample and an ECG signal sample are acquired by the data acquisition unit 26 (FIG. 1) in step 104. The sample acquisition step 104 may be performed at a predetermined frequency, such as on the order of once every millisecond. The ECG signal sample and the blood pressure signal sample are, preferably, simultaneously acquired.

The sample acquisition step 104 is repeated until it is determined in step 108 that a predetermined number of blood pressure samples has been acquired. The predetermined number of samples represents a "large search window" and the time interval represented by the large search window is selected to break down the task of processing of the blood pressure signal in order to achieve signal processing efficiencies while insuring that only a single systole occurs in each such window. In the illustrative embodiment, the large search window represents a time interval approximately equal to the duration of a typical blood pressure pulse (i.e., from time $t_4$–$t_7$ in FIG. 3), such as 0.5 seconds. The large search window interval may be a predefined time interval or, alternatively, may be user selectable and/or adjustable. More particularly, the user may select the time interval of the large search window or the user may input certain information about the patient, such as the patient's body weight, in response to which the large search window interval is computed.

Once a sufficient number of blood pressure signal samples to constitute a large search window have been acquired, a blood pressure signal sample is selected for processing in step 112. As will become apparent, the samples within the large search window are processed to, initially, find a maximum (step 116). During the first iteration of the process, the sample selection defines a point in the middle of the large search window, such that there is sufficient data in memory before and after the point to determine if the point is a systole. During subsequent iterations of the process, the selected sample is the sample following the sample selected during the previous iteration.

Various schemes may be used to select the sample to be processed during the first iteration of the process. In accordance with one method of selecting the first sample for processing, the rise time of a blood pressure pulse, either measured or typical, is used. The rise time determines how far back signal samples must be processed in the event that the selected sample represents a systole. Stated differently, the first sample selected for processing occurs after a time interval equal to at least the rise time of the blood pressure pulse has lapsed.

The blood pressure pulse rise time information may be provided to the processor 14 in various ways. As one example, the user views the blood pressure signal on the display 22, visually determines the rise time and enters this information via the user interface 16. Thus, taking the blood pressure signal 52 (FIG. 2) as an example of what might be displayed, the user viewing the first pulse notes that its rise time is on the order of ($t_5$–$t_4$). Upon entering this information into the monitor 10, the first sample selected for processing in step 112 occurs at time ($t_5$–$t_4$). Alternatively, the typical rise time may be a preselected, default value or may be user adjustable and/or selectable, such as by having the user enter certain information regarding the patient, such as the patient's age and/or body weight.

In step 116, it is determined whether the selected sample is the maximum within a "small search window." Samples within a small search window are processed together in order to enhance the efficiency of signal processing. The selection of the time interval represented by the small search window is a function of many factors, including the speed of the processor 14 and the frequency content of the signal (i.e., the more high-frequency noise associated with the signal, the larger the optimum small search window, in order to reduce the likelihood of false detections). In the illustrative embodiment, the width of the small search window is on the order of 0.1 seconds. The time interval represented by the small search window may be preset or, alternatively, may be user selectable and/or adjustable.

Step 116 comprises multiple iterations during each iteration of the overall process of FIG. 5. The way in which it is determined whether the selected sample is a maximum in the small search window is by comparing its amplitude to that of all samples within the same window. More particularly, upon the first iteration within step 116, when the selected sample in the small search window is being processed, its amplitude is compared with the first value in the small window to determine which is greater. During the second iteration within step 116, the selected sample in the small search window is compared with the second value in the small window to determine which is greater.

In the event that the selected sample is not greater or equal to every sample it is compared to in the small search window, then the process is repeated starting with step 104, as shown. That is, if the processed sample is not a maximum in the small window, then the next sample is acquired, etc. Alternatively, if it is determined in step 116 that the selected sample is the maximum in the small search window, then the time of occurrence and amplitude of the processed sample is stored as the new maximum within the window.

In subsequent step 120, it is determined whether the blood pressure signal fell by at least a predetermined amount during an interval preceding the occurrence of the maximum. In the event that the blood pressure signal did fall by at least the predetermined amount during the interval preceding the maximum, then step 124 is performed in which it is determined whether the blood pressure signal fell by at least a predetermined amount during an interval following the maximum. If both of these queries are answered in the affirmative, then a systole has been located and, in subsequent step 128, the time of the selected sample is stored as that of a systole. Alternatively, if either the blood pressure signal did not fall by at least the predetermined amount during the interval preceding the maximum, or the blood pressure signal did not fall by at least a predetermined amount during the interval following the maximum, then the process is repeated starting at step 104, as shown.

The purpose of steps 120 and 124 is to determine whether the particular large search window in which the selected sample occurs contains a systole. For example, consider the case where the large search window extends from time $t_5$–$t_7$ and the sample at time $t_6$ has been selected for processing in step 112. Processing a small search window centered at time $t_6$ in step 116 reveals that the sample occurring at time $t_6$ is the maximum within that small search window. However, it will subsequently be determined in step 120 that the blood pressure signal did not fall by a predetermined amount during an interval preceding the maximum. This determination will cause the process to be repeated since the maximum at time $t_6$ does not represent a systole.

The predetermined amounts used in steps 120 and 124 may be predefined values, or alternatively, may be user selectable and in both cases, are selected (either by the manufacturer or the user) in order to distinguish a systole from other artifacts in the blood pressure signal. In the illustrative embodiment, the predetermined amount is a value that is selected by the user, on the order of 5 mmHg. Further, the predetermined amounts of steps 120 and 124 may be the same or, alternatively, may be different. In applications in which the predetermined amounts of steps 120 and 124 are user selectable, the selection may be based on the user viewing the blood pressure signal and determining a value suitable for distinguishing a systole from other artifacts or, alternatively, may be based on attributes of the patient which are entered by the user, such as the patient's weight and/or age.

Also stored in step 128, in association with the time of occurrence of each systole, is the amplitude of the systole, the time of the diastole associated with the systole, the amplitude of the diastole and the average blood pressure for the particular beat. In determining the time of the diastole associated with a stored systole, signal samples preceding the time of each stored systole are processed. In one embodiment, the time interval in which the diastole is searched is equal to the rise time of the blood pressure pulse which is provided to the processor 14 in step 112 (FIG. 5). The signal samples preceding a detected systole are processed to detect a minimum until the signal begins to climb again. The average blood pressure for the beat is determined by integrating the blood pressure signal over the time interval between two diastoles. Thereafter, the process terminates in step 130. However, the entire process of FIG. 5 is repeated to find each systole/diastole pair in a collected data sample.

Figure 6:
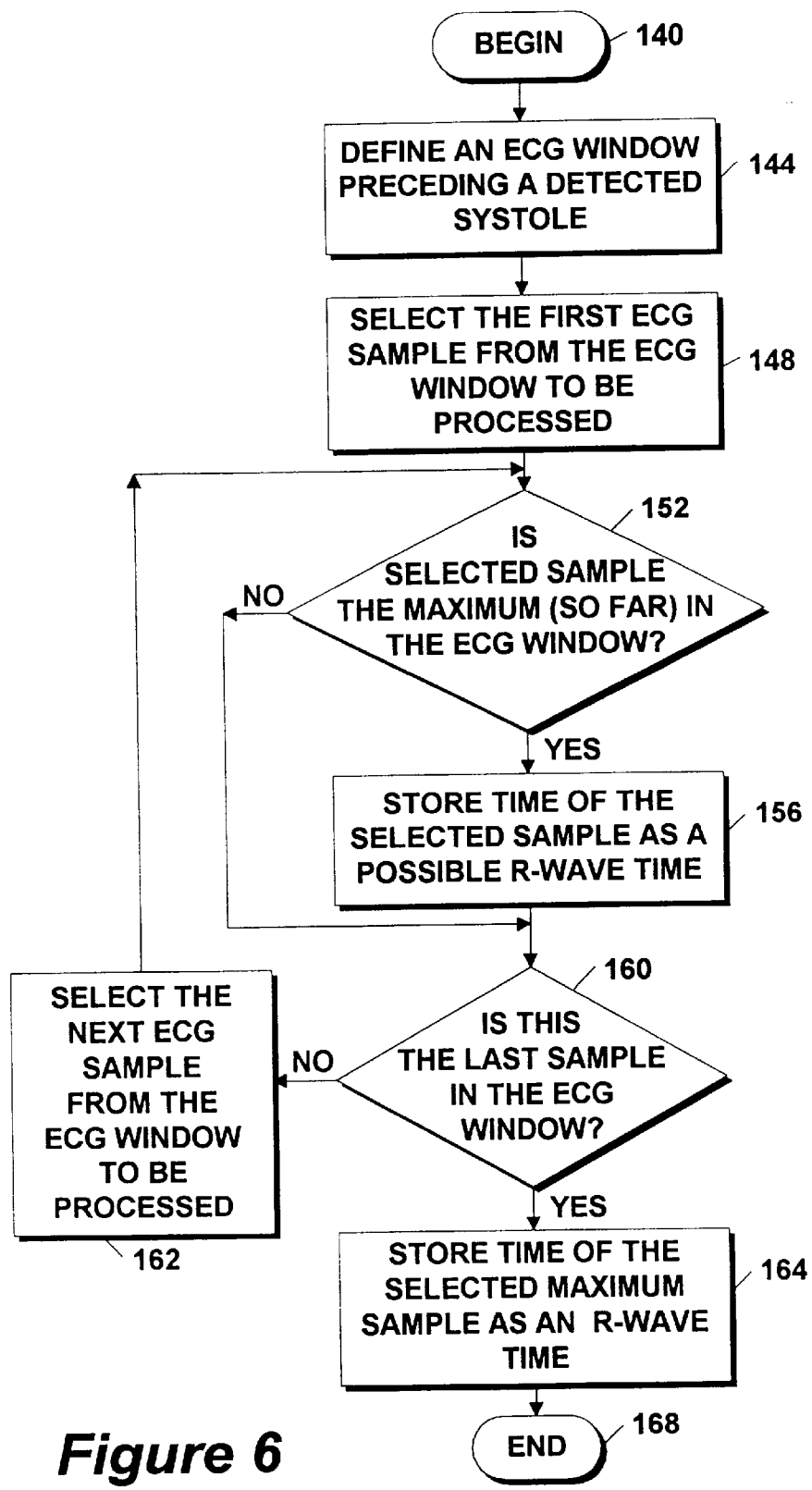
FIG. 6 is a flow diagram illustrating a method of implementing the second stage of R-wave detection of FIG. 4.

The second stage 80 of R-wave detection according to the method of FIG. 4 is shown in FIG. 6. Recall that this stage of processing is responsive to the digitized ECG signal 82 as well as to the stored systole times generated in the first stage 70 of processing. The second stage 80 of processing commences in step 140, following which an ECG window is defined in step 144. The ECG window is a time interval preceding a detected systole time. Thus, this step includes the processor 14 accessing a stored systole time from memory 18 and computing a time interval preceding the stored time. The ECG window represents a time interval during which an R-wave event 56 (FIG. 3) is expected to have occurred and is the interval during which ECG signal samples will be processed to locate an R-wave event. The ECG window thus, commences at a predetermined time prior to the stored systole time and terminates either some time before the stored systole time or at the stored systole time. In the illustrative embodiment, the ECG window commences 250 milliseconds preceding a stored systole time and terminates 25 milliseconds before the stored systole time. Further, the ECG window may be a predefined window (i.e., having a predefined, or default duration and time relationship to a detected systole) or, alternatively, may be user selectable and/or adjustable. As one example, the ECG window duration and time relationship to a systole is computed by the processor 14 in response to certain patient information, such as the patient's size and/or the location from which the blood pressure signal is acquired (e.g., the finger or arm), which is input by the user via the user interface 16.

Once the ECG window is defined in step 144, the first sample from the ECG window is selected for processing in step 148. Subsequently, in step 152, it is determined whether the selected ECG signal is the maximum of the samples in the ECG window. This determination is performed in an iterative manner similar to the maximum determination in step 116 of FIG. 5. That is, the amplitude of the selected sample is compared to the previously processed maximum amplitude within the window to determine whether the selected sample represents a "new" maximum. In the event that the selected sample is not the maximum in the ECG window, then step 160 is next performed, as shown. Alternatively, if the selected sample is the maximum in the ECG window, then the time of the selected sample is stored as a possible R-wave event time in step 156. However, it is not until all samples in the ECG window are processed that a determination can be made as to whether the possible R-wave event time represents an actual R-wave event time. Thus, in subsequent step 160, it is determined whether the processed sample is the last sample in the ECG window. If this is not the case, then step 162 is performed in which the next ECG signal sample from the ECG window is selected for processing, following which the process is repeated starting at step 152 until the last sample has been processed. Once the last sample has been selected for processing, then the time of the selected sample representing the maximum in the ECG window is stored as the time of an R-wave event in step 164. Thereafter, the process terminates in step 168.

With the above method and apparatus, the precise times of R-wave events are determined from digitized ECG and blood pressure signals to a precision determined by the data sampling rate, for example, to within approximately 0.001 seconds for a data sampling rate of 0.001 seconds per sample. The first stage of processing (FIG. 5) is used to determine the times of systoles within the blood pressure signal and, this information is used in the second stage of processing (FIG. 6) to define an ECG window of the ECG signal during which the R-wave event occurs. Having defined the ECG window, samples of the ECG signal within the ECG window are processed in a manner that ensures that the precise R-wave event time is determined.

Figure 7:
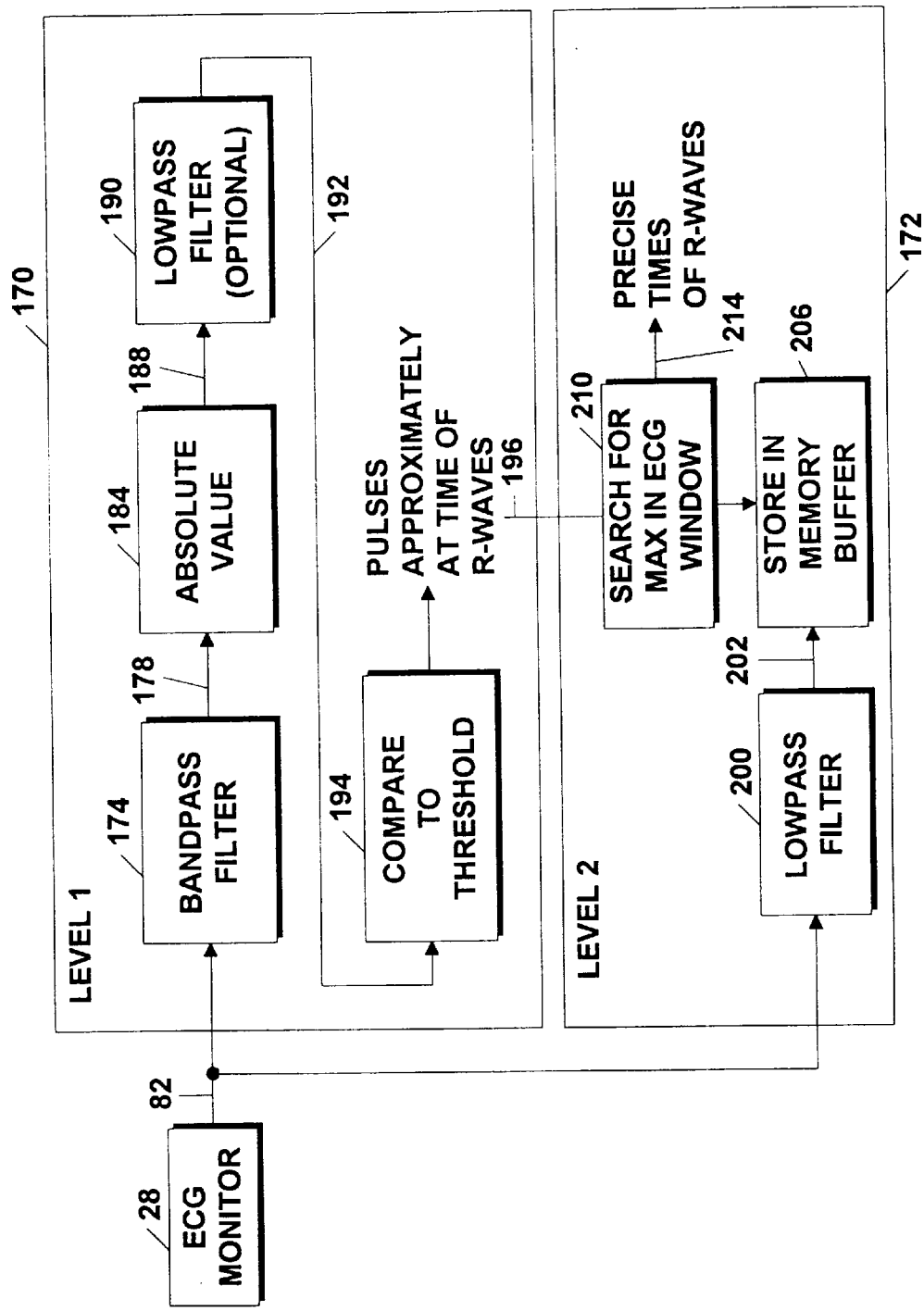
FIG. 7 is a block diagram of an alternative process of R-wave detection in response to an ECG signal according to the invention.

Referring to FIG. 7, an alternative R-wave detection scheme is illustrated. The R-wave detection of FIG. 7 is achieved without use of the patient's blood pressure signal and is responsive only to the ECG signal 82 provided by the ECG monitor 28 (FIG. 1). The R-wave detection of FIG. 7 includes two stages of processing 170, 172. In accordance with the first stage 170, the digitized ECG signal 82 is filtered by a bandpass filter 174 to provide a filtered ECG signal 178. Since the feature of interest in the ECG signal is the R-wave event, which is typically accompanied by frequency content on the order of 17 Hz+/−3 Hz, in the illustrative embodiment, the bandpass filter 174 has a nominal center frequency of 17.0 Hz and a pass band of approximately 6 Hz.

The absolute value of the filtered ECG signal 178 is calculated in step 184. By taking the absolute value of the filtered ECG signal, all of the stored samples of the ECG signal are positive. The positive-going pulses 188 may, optionally, be lowpass filtered in step 190, as shown, in order to attenuate noise due to brief episodes of 17 Hz noise to provide a further filtered signal 192.

In a process step 194, each of the ECG signal samples is compared to a threshold level. If a processed signal sample exceeds the threshold level, then the time of that sample is stored as an approximate R-wave time. Alternatively, the time of the sample is not stored. Thus, the output of the comparison step 194 is a set 196 of stored times of signal samples which correspond to approximate R-wave times. The threshold level used in step 194 may be a predetermined value and/or may have a predefined relationship to "recent" previously processed signal samples. In one embodiment, the threshold level is a predetermined percentage of the average peak values of recent signal samples. Before a sufficient number of signal samples are processed to determine the threshold level, it may be desirable to store a short period of lowpass filtered ECG signal samples processed by steps 174 to 190 and set the threshold level to a percentage of the average peak values of the signal 192 during that period.

The second stage 172 of R-wave detection relies on the approximate R-wave times provided at the output 196 of the first processing stage 170 and, further, on the digitized ECG signal 82. The digitized ECG signal 82 is lowpass filtered in a step 200, preferably by a filter that preserves time-domain content of the signal, such as a filter having an "elliptical" response. The filtered signal samples 202 are stored in memory in step 206. In a process step 210, the approximate R-wave times 196 provided by the first stage 170 of R-wave detection are used to define an ECG window within the filtered signal portion stored in step 206 for processing to determine the precise times of R-waves. More particularly, an ECG window is defined to have a predetermined time relationship with respect to each approximate R-wave time and a predetermined duration. The stored samples are accessed and processed in groups defined by ECG windows which have a predetermined time relationship with respect to the approximate R-wave times determined in stage 170. The maximum signal sample within each ECG window yields a precise R-wave time at the output 214 of the second stage 172 of R-wave detection.

Figure 8:
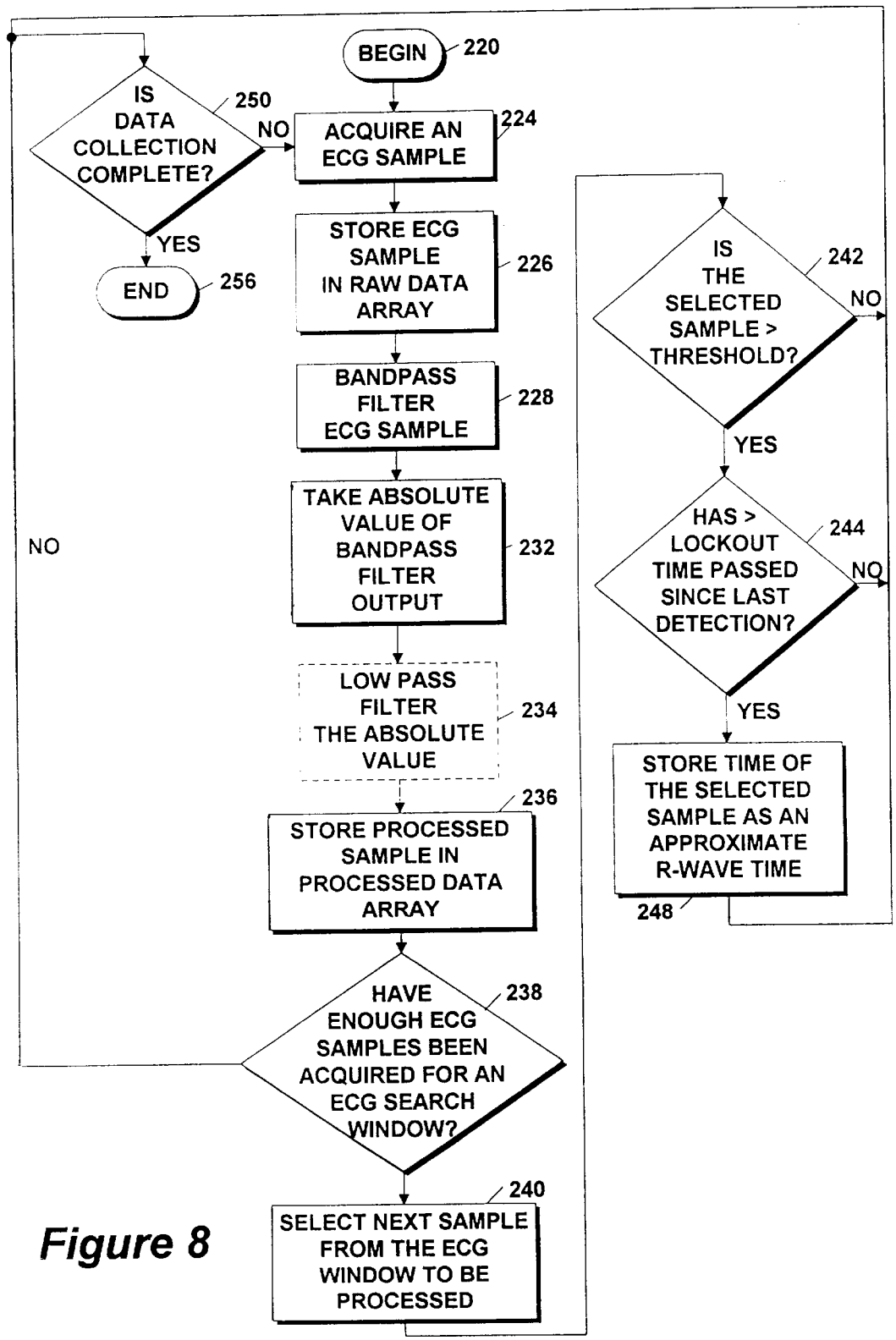
FIG. 8 is a flow diagram illustrating a method of implementing the first stage of R-wave detection of FIG. 7.
Figure 9:
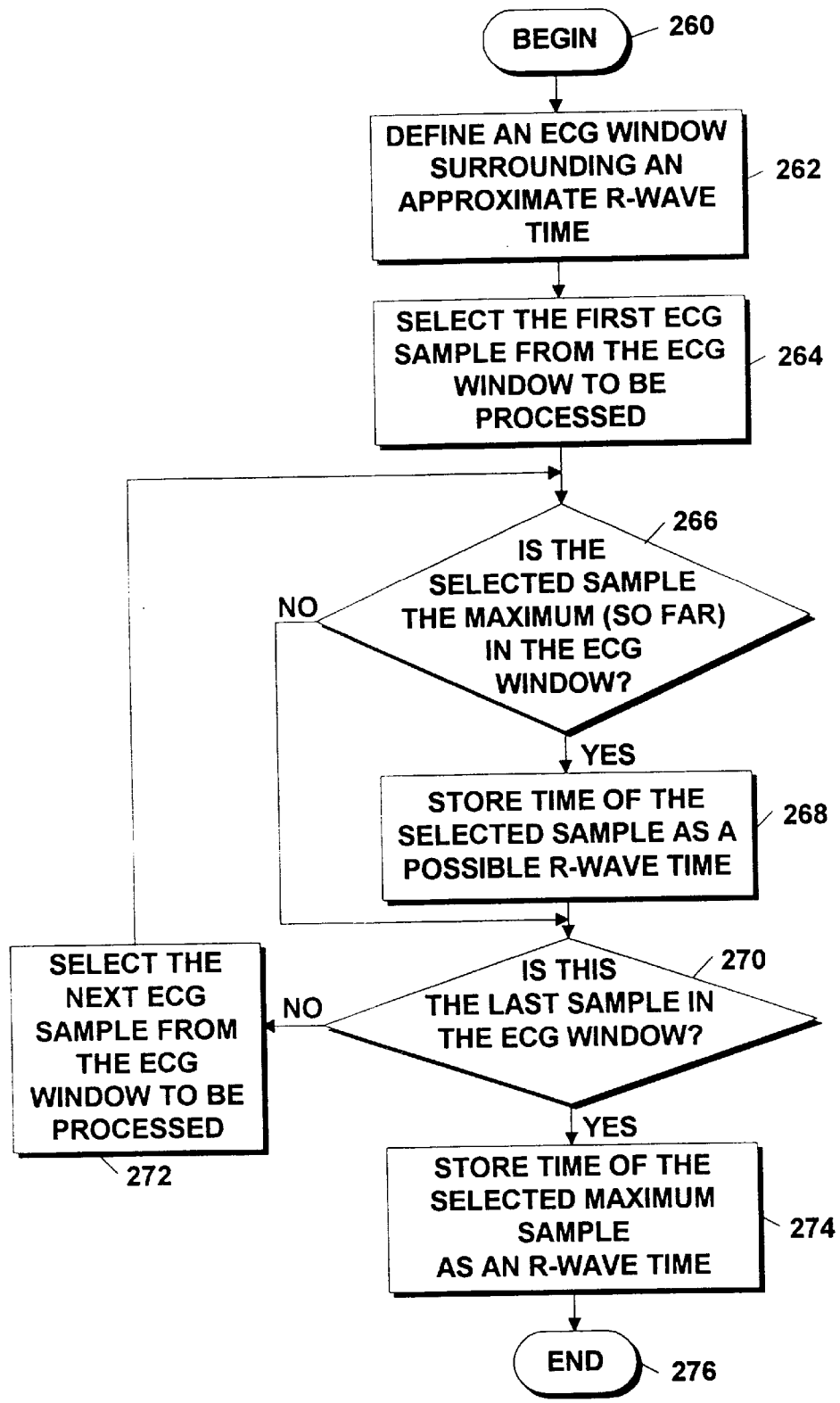
FIG. 9 is a flow diagram illustrating a method of implementing the second stage of R-wave detection of FIG. 7.

The process of FIG. 7 is described in more detail in conjunction with the flow diagrams of FIGS. 8 and 9. FIG. 8 illustrates a method of implementing the first stage 170 of R-wave detection and FIG. 9 illustrates a method of implementing the second stage 172 of R-wave detection.

Referring to FIG. 8, the process commences in step 220, following which an ECG signal sample is acquired by the data acquisition unit 26 (FIG. 1) in step 224. In step 226, the acquired ECG signal sample is stored in a raw data array. Thereafter, in step 228, the stored ECG signal sample is bandpass filtered. Various apparatus and methods are suitable for filtering the ECG signal sample in step 228, including a software filter.

In subsequent step 232, the absolute value of the processed signal sample is computed, to ensure that all pulses are positive-going. Optionally, the sample may be lowpass filtered in step 234. Subsequently, in step 236, the processed signal sample is stored in a processed data array.

In process step 238, it is determined whether a predetermined number of ECG signal samples have been acquired. The predetermined number is associated with an ECG signal processing window of sufficient width to contain an R-wave event. In the illustrative embodiment, the predetermined number of samples are those acquired within an interval on the order of 0.2 seconds. In the event that the predetermined number of samples has not been acquired, then it is determined in step 250 whether data collection has been completed. If data collection has been completed, then the process terminates in step 256. Alternatively, the process is repeated, starting with acquisition of another ECG signal sample in step 224, as shown.

If it is determined in step 238 that enough signal samples have been acquired to comprise an ECG search window, then the next sample in the ECG window is selected for processing in step 240 and, it is next determined in process step 242 whether the selected sample exceeds a threshold level. In the illustrative embodiment, the selected sample precedes the most recently acquired sample by a predetermined time. As will become apparent, each processed sample is compared to the threshold level to determine whether the sample exceeds the threshold and thus, is indicative of an approximate R-wave time. The threshold level may be a predefined, or predetermined level, it may be a function of the amplitude of certain ECG signal samples or it may be user selectable or adjustable. In the illustrative embodiment, the threshold level is a predetermined percentage of the average peak values of a predetermined number of recently processed (steps 224 through 236) ECG signal samples. A suitable number of ECG signal samples from which to compute the threshold value is on the order of five or more and the predetermined percentage of the average peak values is on the order of 30%.

Prior to a certain number of iterations of the process of FIG. 8, however, the predetermined number of ECG signal samples on which to base the threshold level will not yet have been processed. During this time, a predetermined threshold level may be used or processing may be delayed until after the predetermined number of samples have been accumulated.

In the event that it is determined in step 242 that the selected signal sample is not greater than the threshold level, then step 250 is next performed, as shown. Alternatively, it is next determined in step 244 whether a lockout time interval has lapsed since the last detection of a selected sample exceeding the threshold. The lockout time interval is selected to prevent noise from causing false R-wave detections. In the illustrative embodiment, the lockout time interval is on the order of 0.2 seconds. In the event that the lockout time interval has not lapsed, then the process is repeated starting at step 250. Alternatively, the time of occurrence of the selected sample is stored in step 248 as the approximate time of an R-wave event, following which step 250 is repeated.

Referring to FIG. 9, the second stage 172 of R-wave detection according to the process of FIG. 7 commences in step 260, following which an ECG window is defined in step 262. The ECG window is a portion of the digitized and stored ECG signal during which an R-wave event is expected to occur. In the illustrative embodiment, the ECG window has a predefined time relationship centered around an approximate R-wave location stored in step 248 of FIG. 8 and a duration on the order of 0.15 seconds. It will be appreciated by those of ordinary skill in the art however, that more generally, the ECG window may be defined in other manners and, in fact, may be user selectable in terms of its duration and relationship to an approximate R-wave time stored in step 248.

In subsequent step 264, the first sample of the digitized ECG signal in the ECG window is selected for processing. Thereafter, in step 266, it is determined whether the selected sample is the maximum of the samples that have been processed within the ECG window. As discussed previously, this determination is made by comparing the selected sample with the previously processed signal sample having the greatest amplitude in the ECG window.

In the event that the selected signal sample is not the maximum within the ECG window, then step 270 is next performed in which it is determined whether the selected sample is the last sample of the ECG window. Alternatively, the time of the selected sample is stored in step 268 as the time of a possible R-wave event. In step 270, if it is determined that the selected sample is not the last sample within the ECG window, then step 272 is performed in which the next ECG sample from the ECG window is selected for processing, following which the process is repeated starting at step 266, as shown. Alternatively, the time of the selected sample is stored as the time of an R-wave event in step 274, following which the process terminates in step 276.

As will now be apparent, the embodiments of the present invention include defining a relatively narrow ECG window of the ECG signal in which the R-wave events occur. The samples within the defined ECG windows are processed in a manner which provides a precise determination of R-wave events. The precision of the R-wave event detection is made possible by the definition and precise processing within the relatively narrow ECG windows in which R-wave events occur, since such precise processing of the entire ECG signal is computationally intensive and more liable to be affected by artifacts, such as noise, lead movement, muscle movement, etc.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A method of detecting the time of occurrence of the peak of an R-wave of an ECG signal of a patient, comprising the steps of:
    storing the ECG signal of the patient;
    approximating the time of occurrence of the peak of the R-wave in response to the stored ECG signal; and
    determining the precise time of occurrence of the peak of the R-wave in response to the approximated time of occurrence of the peak of the R-wave.

2. The method of claim 1 wherein the approximating step includes:
    comparing samples of the stored ECG signal within a first window to a threshold level; and
    storing the time of occurrence of a sample exceeding said threshold level as the approximate time of occurrence of the peak of the R-wave.

3. The method of claim 2 further comprising the step of determining the threshold level by computing a percentage of the average peak values of samples of the stored ECG signal.

4. The method of claim 2 wherein the determining step includes:
    searching a second window of the stored ECG signal preceding the first window for a maximum; and
    storing the time of the maximum as the precise time of occurrence of the peak of the R-wave.

5. Apparatus for detecting the time of occurrence of the peak of an R-wave of an ECG signal of a patient comprising:
    a memory for storing the ECG signal of the patient; and
    a processor responsive to the stored ECG signal for approximating the time of occurrence of the peak of the R-wave and for determining the precise time of occurrence of the peak of the R-wave in response to the approximate time of occurrence of the peak of the R-wave.

6. The apparatus of claim 5 wherein the processor includes a first processor portion for approximating the time of occurrence of the peak of the R-wave in response to the stored ECG signal and a second processor portion for determining the precise time of occurrence of the peak of the R-wave in response to the approximate time of occurrence of the peak of the R-wave and the stored ECG signal.

7. The apparatus of claim 6 wherein the first processor portion includes:
    a detector for detecting the time of occurrence of a sample of the stored ECG signal occurring within a first window of the stored ECG signal exceeding a threshold level; and
    a storage mechanism for storing the the time of occurrence of the sample exceeding the threshold level in the memory as an approximate time of occurrence of the peak of the R-wave.

8. The apparatus of claim 7 wherein the second processor portion includes a detector for detecting a maximum of the stored ECG signal occurring during a second window of the stored ECG window preceding the first window, wherein the time of the maximum is stored in the memory as a precise time of occurrence of the peak of the R-wave.

9. A method of detecting the time of occurrence of the peak of an R-wave of an ECG signal of a patient, comprising the steps of:
    accumulating a plurality of samples of the ECG signal of the patient;
    defining an ECG window comprising a predetermined number of the accumulated samples of the ECG signal;
    processing each sample comprising the ECG window to determine a maximum within the ECG window; and
    storing the time of occurrence of the maximum as the time of occurrence of the peak of the R-wave.

10. The method of claim 9 further comprising the steps of:
    accumulating a plurality of samples of a blood pressure signal of the patient;
    defining a systole window comprising a predetermined number of the accumulated samples of the blood pressure signal; and
    processing each sample comprising the systole window to determine the time of occurrence of a systole, wherein the ECG window defining step includes defining the ECG window to have a predetermined time relationship to the time of occurrence of the systole.

11. The method of claim 9 further comprising the step of approximating the time of occurrence of the peak of the R-wave and the ECG window defining step includes defining the ECG window to have a predetermined time relationship to the approximate time of occurrence of the peak of the R-wave.

12. A method of detecting times of occurrence of a plurality of R-waves of an ECG signal of a patient, comprising the steps of:

(a) storing the ECG signal of a patient;
(b) approximating the times of occurrence of the R-waves in response to the stored ECG signal, comprising the steps of:
　(i) comparing samples of the stored ECG signal within a first window to a threshold level; and
　(ii) storing the time of occurrence of a sample exceeding said threshold level as an approximate R-wave time; and
(c) determining the precise times of occurrence of the R-waves in response to the approximated times of the R-waves, comprising the steps of:
　(i) searching a second window of the stored ECG signal preceding the first window for a maximum; and
　(ii) storing the time of the maximum as the precise R-wave time.

13. Apparatus for detecting times of occurrence of a plurality of R-waves of an ECG signal of a patient comprising:
(a) a memory for storing the ECG signal of the patient; and
(b) a processor responsive to the stored ECG signal for approximating the times of occurrence of the R-waves and for determining the precise times of occurrence of the R-waves in response to the approximate times of the R-waves, said processor including a first processor portion for approximating the times of occurrence of the R-waves in response to the stored ECG signal and a second processor portion for determining the precise times of the R-waves in response to the approximate R-wave times and the stored ECG signal, said first processor portion including:
　(i) a detector for detecting the time of occurrence of a sample of the stored ECG signal occurring within a first window of the stored ECG signal exceeding a threshold level; and
　(ii) a storage mechanism for storing the time of occurrence of the sample exceeding the threshold level in the memory as an approximate R-wave time; and
said second processor portion including a detector for detecting a maximum of the stored ECG signal occurring during a second window of the stored ECG window preceding the first window, wherein the time of the maximum is stored in the memory as a precise R-wave time.

* * * * *

UNITED STATES PATENT AND TRADEMARK OFFICE
CERTIFICATE OF CORRECTION

PATENT NO : 5,984,954
DATED : November 16, 1999
INVENTOR(S) : Cohen

It is certified that error appears in the above-identified patent and that said Letters Patent are hereby corrected as shown below:

On the Title page, under the "Inventor" section, delete "Arlington" and replace it with --Newton--.

under the "Attorney, Agent, or Firm" section, delete "Daly, Crowly & Mofford,LLP and replace it with --Daly, Crowley & Mofford, LLP--

Col. 12 line 34 (Claim 8) delete "a" and replace it with --the--.

Signed and Sealed this

Twenty-fourth Day of April, 2001

Attest:

NICHOLAS P. GODICI

Attesting Officer

Acting Director of the United States Patent and Trademark Office